United States Patent
Merenov et al.

(10) Patent No.: US 9,080,005 B2
(45) Date of Patent: *Jul. 14, 2015

(54) PROCESS FOR THE PRODUCTION OF METHYLENE DIPHENYL DIISOCYANATE ISOMER MIXTURES WITH HIGH 2,4'-METHYLENE DIPHENYL DIISOCYANATE PURITY

(71) Applicants: Andrei S. Merenov, Lake Jackson, TX (US); Gerard I. Jansma, Krewerd (NL); Paul A. Gillis, Lake Jackson, TX (US)

(72) Inventors: Andrei S. Merenov, Lake Jackson, TX (US); Gerard I. Jansma, Krewerd (NL); Paul A. Gillis, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/347,764

(22) PCT Filed: Nov. 19, 2012

(86) PCT No.: PCT/US2012/065779
§ 371 (c)(1),
(2) Date: Mar. 27, 2014

(87) PCT Pub. No.: WO2013/081873
PCT Pub. Date: Jun. 6, 2013

(65) Prior Publication Data
US 2014/0264163 A1    Sep. 18, 2014

Related U.S. Application Data

(60) Provisional application No. 61/565,315, filed on Nov. 30, 2011.

(51) Int. Cl.
C08G 18/76 (2006.01)
C07C 263/10 (2006.01)
C07C 263/20 (2006.01)

(52) U.S. Cl.
CPC .......... C08G 18/7671 (2013.01); C07C 263/10 (2013.01); C07C 263/20 (2013.01)

(58) Field of Classification Search
None
See application file for complete search history.

(56) References Cited

U.S. PATENT DOCUMENTS 7,495,124 B2 *  2/2009  Pirkl et al. ............... 560/352
7,521,576 B2 *  4/2009  Schal et al. .............. 558/420

(Continued)

FOREIGN PATENT DOCUMENTS

WO    2010040675 A2    4/2010

OTHER PUBLICATIONS

Database Caplus Chemical Abstracts Service, Columbus, Ohio, US; Database Accession No. 2003:736411, Abstract of Stepanski et al., Polyurethanes Conference 2002, Conference Proceedings, Salt Lake City, UT, United States, Oct. 13-16, 2002, 594-600.*

(Continued)

*Primary Examiner* — Karl J Puttlitz

(57) ABSTRACT

The present invention includes a process and apparatus for the production of methylene diphenyl diisocyanate (MDI) isomer mixtures with a low 2,2'-MDI isomer content and a high 2,4'-MDI isomer content. The resulting mixtures have an increased reactivity and are acceptable in food grade application due to the reduction in primary aromatic amines formed during the curing process. The process and apparatus also include controlling the amount of 4,4'-MDI, which is the most reactive isomer in the mixture allowing use in a wide variety of applications.

10 Claims, 2 Drawing Sheets

(56) References Cited

U.S. PATENT DOCUMENTS

| | | |
|---|---|---|
| 7,649,108 B2 * | 1/2010 | Schal et al. ............ 560/352 |
| 2004/0171869 A1 * | 9/2004 | Reif et al. ............ 560/347 |
| 2006/0173206 A1 | 8/2006 | Schal et al. |
| 2007/0117997 A1 | 5/2007 | Keggenhoff et al. |
| 2008/0275269 A1 | 11/2008 | Keggenhoff et al. |
| 2011/0224456 A1 | 9/2011 | Koole et al. |
| 2013/0172604 A1 | 7/2013 | Merenov et al. |
| 2013/0172605 A1 | 7/2013 | Bhattacharyya et al. |

OTHER PUBLICATIONS

PCT/US2012/065779, International Search Report/Written Opinion of the International Searching Authority issued Jan. 17, 2013.

PCT/US2012/065779, International Preliminary Report on Patentability issued on Jun. 3, 2014.

* cited by examiner

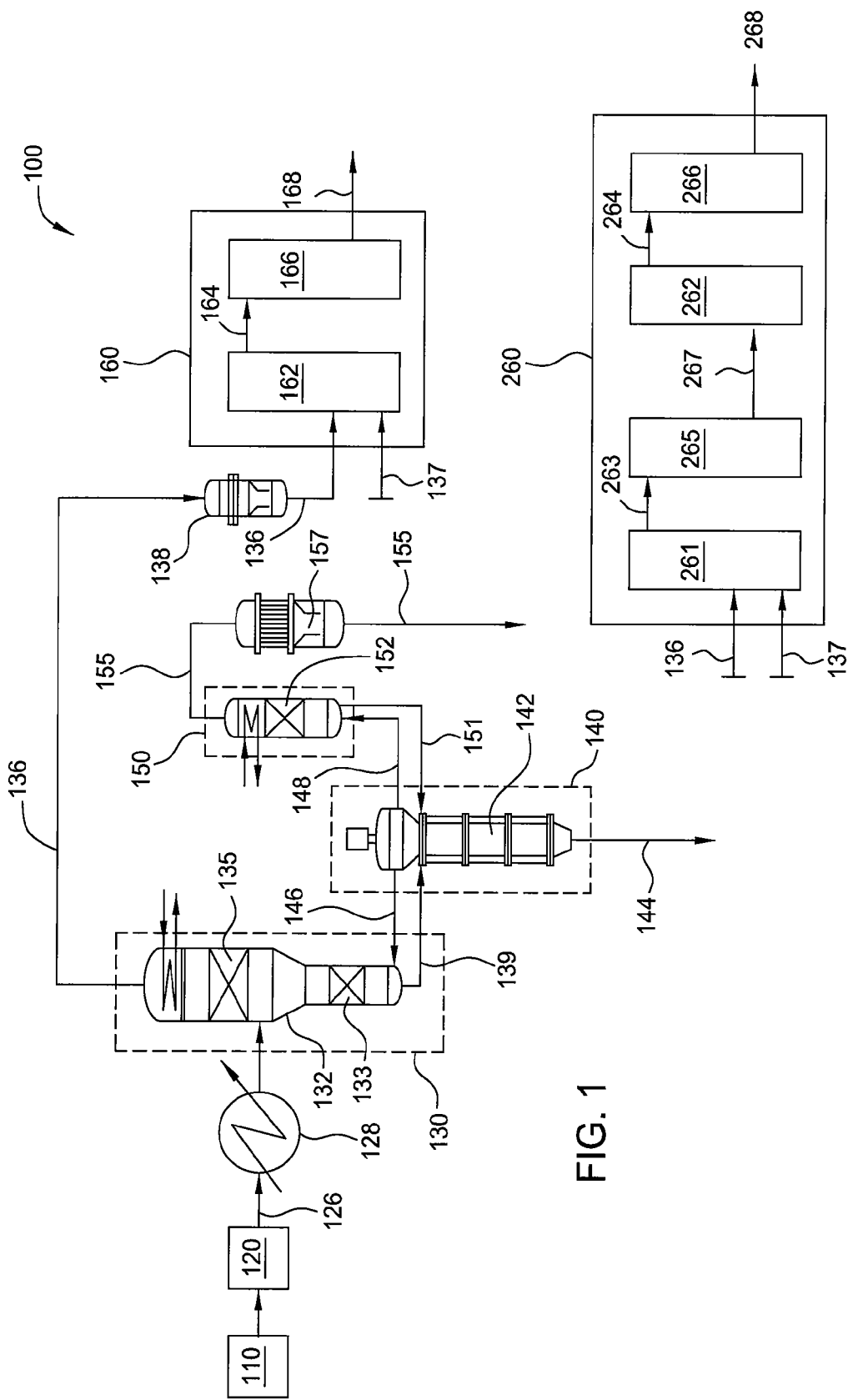

PROCESS FOR THE PRODUCTION OF METHYLENE DIPHENYL DIISOCYANATE ISOMER MIXTURES WITH HIGH 2,4'-METHYLENE DIPHENYL DIISOCYANATE PURITY

BACKGROUND OF THE INVENTION

1. Field of the Invention

Embodiments of the present invention generally relate to a process and apparatus for the production of methylene diphenyl diisocyanate (MDI) isomer mixtures with low 2,2'-MDI isomer content and high 2,4'-MDI isomer content.

2. Description of the Related Art

Mixtures of methylene diphenyl diisocyanate (MDI) isomers are widely used in the preparation of polyurethane film composites and adhesives. During the preparation of film composites or adhesives, an MDI mixture reacts with a polyol (e.g., polyether polyol) to form polyurethane. Generally, an excess of MDI is used to ensure the completion of the reaction. However, non-reacted MDI can diffuse to the surface of the film composite or adhesive, where it may be hydrolyzed into a primary aromatic amine. This creates a problem in certain applications, such as product packaging in the food industry because there are strict requirements regulating the amount of primary aromatic amines in food packaging materials.

Conventional MDI processes produce three isomers, i.e., 4,4'-MDI, 2,4'-MDI, and 2,2'-MDI. Other products of conventional MDI processes are heavier molecular weight isocyanates, commonly called polymeric MDI (PMDI). The most reactive MDI isomer is 4,4'-MDI, and the least reactive is 2,2'-MDI. Thus, among MDI isomers, 2,2'-MDI requires the longest time for conversion, and the overall reactivity of an MDI isomer mixture increases as the 2,2'-MDI isomer content is reduced. However, the ratio of 2,2'-MDI and 2,4'-MDI to 4,4'-MDI also controls the viscosity of the prepolymer. That is, prepolymer viscosity decreases as the ratio of 2,2'-MDI and 2,4'-MDI to 4,4'-MDI increases. Thus, mixtures with a high amount of 2,4'-MDI and a low amount of 2,2'-MDI are used in applications requiring low viscosity prepolymers, particularly in the food industry.

Therefore, as the demand for low viscosity prepolymers increases, such as for food applications, there is a need for improved methods and apparatus for producing MDI isomer mixtures with low 2,2'-MDI content and high 2,4'-MDI content.

SUMMARY OF THE INVENTION

In one embodiment, a process for the production of a mixture of methylene diphenyl diisocyanate (MDI) isomers comprises forming methylene diphenyl diamines and polyamines of the diphenylmethane series by reacting aniline and formaldehyde in the presence of an acid catalyst, phosgenating the methylene diphenyl diamines and polyamines of the diphenylmethane series to produce a mixture of the MDI isomers and polymeric MDI, separating from the mixture of the MDI isomers and the polymeric MDI a first fraction containing at least 98% by weight of the MDI isomers comprising at least 56% by weight of 2,4'-MDI and 2,2'-MDI based on the total weight of the first fraction, and separating from the first fraction a second fraction containing at least 99% by weight of the MDI isomers comprising at least 95% by weight of 2,4'-MDI based on the total weight of the second fraction.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 1 is a schematic depiction of an apparatus and process according to one embodiment.

FIG. 2 is a schematic depiction of a crystallization section according to one embodiment.

DETAILED DESCRIPTION

Figure 3:
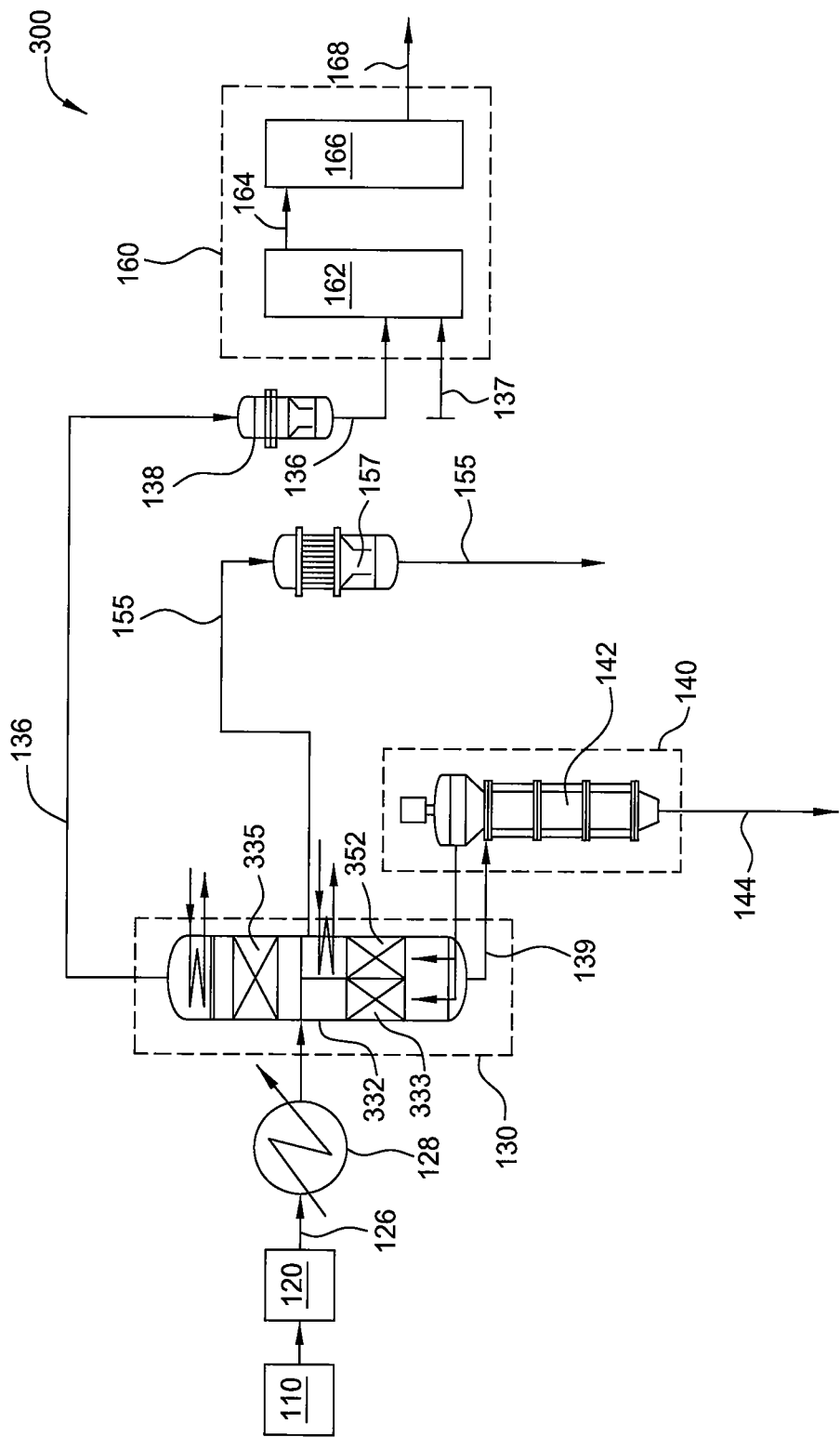
FIG. 3 is a partial schematic depiction of an apparatus and process according to another embodiment.

Embodiments of the present invention generally relate to a process and apparatus for the production of methylene diphenyl diisocyanate (MDI) isomer mixtures with low 2,2'-MDI isomer content and high 2,4'-MDI isomer content. The resulting mixtures have an increased reactivity and are acceptable in food grade applications due to the reduction in primary aromatic amines formed during the curing process. The process and apparatus also include controlling the amount of 4,4'-MDI, which is the most reactive isomer in the mixture allowing use in a wide variety of applications.

FIG. 1 is a schematic depiction of an apparatus and process 100 according to one embodiment. At box 110, a poly amine or poly amine mixture of a diphenylmethane series is formed conventionally by condensing aniline and formaldehyde in the presence of an acid catalyst. Suitable polyamine mixtures of the diphenylmethane series are obtained by condensation of aniline and formaldehyde in a quantitative molar ratio from about between about 20:1 and about 1.6:1 and a quantitative ratio of aniline to acid catalyst from between about 20:1 and about 1:1.

Generally formaldehyde is used as an aqueous solution with water content between about 1% and about 95% by weight, based on the total weight of the solution. Alternatively, other compounds supplying methylene groups (e.g., polyoxymethylene glycol, para-formaldehyde, and trioxane) may be used.

Strong acids, particularly inorganic acids, are suitable as acid catalysts for the reaction of the aniline and formaldehyde. Suitable acids include hydrochloric acid, sulfuric acid, phosphoric acid, and methane sulfonic acid. Solid acid catalysts, such as organic and inorganic ion exchangers, acid silicon/aluminum mixed oxides, and acid zeolites may also be used.

In one embodiment, aniline and the acid catalyst are first mixed together. The mixture of aniline and the acid catalyst are then mixed with formaldehyde at temperatures between about 20° C. and about 100° C., and a preliminary reaction is carried out.

Alternatively, aniline and formaldehyde are first mixed at temperatures between about 5° C. to about 100° C. in the absence of the acid catalyst. In such an example, condensation products of aniline and formaldehyde are formed (i.e., aminal). On completion of the condensation product formation, water present in the reaction mixture may be removed by phase separation or by other suitable procedures, such as distillation. The condensation product is then mixed with an acid catalyst, and a preliminary reaction is carried out at a temperature of about 20° C. to about 100° C.

In either case, the temperature of the reaction mixture is then raised, either in stages or continuously, to a temperature of from about 100° C. to about 250° C. The reaction mixture is then neutralized with a base, such as hydroxides of alkali metals and alkaline earth metals (e.g., sodium hydroxide).

After neutralization, the organic phase is separated from the aqueous phase by suitable methods. The product that contains the organic phase remaining after the separation of the aqueous phase is subjected to a wash procedure to form a purified organic phase. The purified organic phase is then removed from excess aniline and other substances present in the mixture by suitable physical separation methods, such as distillation, extraction, or crystallization.

The polyamine of the diphenyl methane series obtained from the process associated with box 110 is then conventionally reacted with phosgene in an inert organic solvent to form corresponding isocyanates in box 120. Suitable inert solvents include chlorinated, aromatic hydrocarbons, such as monochlorobenzene, dichlorobenzenes, trichlorobenzenes, corresponding toluenes and xylenes, as well as chloroethybenzene. The phosgenation is carried out at temperatures from about 50° C. to about 250° C. and at pressures ranging from ambient pressure to about 50 bar.

After phosgenation, the excess phosgene, any inert organic solvent, the HCL formed, and/or mixtures thereof, are separated from the reaction mixture, such as by distillation. As a result, a crude diisocyanate and polyisocyanate (i.e., crude MDI feedstock 126) is obtained in box 120.

Next, the crude MDI feedstock 126, containing both methylene diphenyl diisocyanate (MDI) isomers and polymeric methylene diphenyl diisocyanate (PMDI) is heated to a temperature of between about 170° C. and about 260° C. in a heat exchanger 128. Generally, in box 130, the lower boiling point components (i.e., 2,2'-MDI and 2,4'-MDI) are separated from the higher boiling point components (i.e., 4,4'-MDI and PMDI). In one embodiment of box 130, the preheated feedstock enters a distillation column 132. The distillation column 132 includes both a stripping section 133 and a rectification section 135. In one embodiment, the stripping section 133 is maintained at a temperature between about 100° C. and about 260° C. and a pressure between about 0.6 mmHg and about 50 mmHg. The rectification section 135 may be maintained at a temperature between about 50° C. and about 200° C. and a pressure between about 0.5 mmHg and about 20 mmHg.

The lower boiling point components, i.e., 2,2'-MDI and 2,4'-MDI, are recovered above the stripping section 133 of the distillation column 132 after purification in the rectification section 135 of the distillation column 132. As a result, a 2,4'-MDI rich mixture 136 exits the distillation column 132 and passes through a condenser 138. The 2,4'-MDI rich mixture 136 has a fraction containing at least 98% by weight of MDI isomers with a content of at least 56% by weight of a mixture of 2,4'-MDI and 2,2'-MDI based on the total weight of the fraction. In one embodiment, the 2,4'-MDI rich mixture 136 has a fraction containing at least 98% by weight of MDI isomers with a content of 4,4'-MDI of from 20% to 43% by weight, a content of 2,4'-MDI of from 56% to 80% by weight, and a content of 2,2'-MDI of from 0.01% to 10% by weight.

The mixture of the higher boiling point components (i.e., 4,4'-MDI and PMDI) are removed from the distillation column 132 as bottoms 139 and passed through an evaporative reboiler 142 at box 140. The evaporative boiler 142 is maintained at a temperature between about 100° C. and about 260° C. and a pressure between about 3 mmHg and about 50 mmHg. The bottom product of the evaporative boiler 142 is PMDI with a reduced amount of MDI isomers and is removed from the evaporative reboiler 142 as a PMDI stream 144. The PMDI stream 144 can be used as a component in rigid and flexible polyurethane foam applications. In the evaporative reboiler 142, a portion of the mixture is evaporated, and a portion of the vapors is returned to the distillation column 132 as a boil-up stream 146.

The remainder of the vapors exits the evaporative reboiler 142 as stream 148, where it enters a side rectifier 152 at box 150. The side rectifier 152 is maintained at a temperature between about 50° C. and about 260° C. and a pressure between about 1 mmHg and about 49 mm Hg. In the side rectifier 152, 4,4'-MDI is separated from traces of PMDI remaining in the vapor. As a result, a purified 4,4'-MDI stream 155 exits the side rectifier 152 and is passed through a quench condenser 157 at a temperature between about 40° C. and about 50° C. The purified 4,4'-MDI stream 155 includes at least 98% by weight content of 4,4'-MDI. In one embodiment, the purified 4,4'-MDI stream 155 has a content of 4,4'-MDI of from 98% to 99.99% by weight, a content of 2,4'-MDI of from 0.001% to 2% by weight, and a content of 2,2'-MDI of from 0.001% to 1% by weight. Bottoms 151 from the side rectifier 152 are recycled into the evaporative reboiler 142.

The 2,4'-MDI rich mixture 136 enters a crystallizing section 160. The crystallizing section 160 may include a single crystallizer that may be a melt crystallizer, a continuous piston column crystallizer, or other industrially available crystallizer. In one embodiment, an additional 2,4'-MDI rich mixture 137 also enters the crystallizing section 160. The additional 2,4'-MDI rich mixture 137 may have a fraction containing at least 99% weight of MDI isomers with a content of 4,4'-MDI of from 1% to 5% weight, a content of 2,4'-MDI of from 30% to 95% weight, and a content of 2,2'-MDI of from 20% to 74% weight.

In one embodiment, the 2,4'-MDI rich mixture 136, and optionally the 2,4'-MDI rich mixture 137, is cooled to a temperature of between about 20° C. and about 28° C. in a crystallizer 162 to form a slurry 164 of purified 2,4'-MDI crystals in a liquid having a composition of about 30% by weight MDI. The slurry 164 enters a separator 166 (e.g., wash column), where the purified 2,4'-MDI crystals are separated from the liquid. The purified 2,4'-MDI crystals are then heated to a temperature of between about 40° C. and about 50° C. to produce a purified 2,4'-MDI stream 168. As a result, the purified 2,4'-MDI stream 168 includes a content of 2,4'-MDI of at least 95% by weight. In one example, the purified 2,4'-MDI stream 168 has a fraction containing at least 99% weight of MDI isomers with a content of 4,4'-MDI of from 0.001% to 5% weight, a content of 2,4'-MDI of from 95% to 99.998% weight, and a content of 2,2'-MDI of from 0.0001% to 0.1% weight. A prepolymer produced from the purified 2,4'-MDI stream 168 has low viscosity and can be used in applications requiring low 2,2'-MDI content, such as polyurethane film composites and adhesives for product packaging in the food industry.

FIG. 2 depicts another embodiment of a crystallizing section 260 in which the 2,4'-MDI rich mixture 136, and optionally the 2,4'-MDI rich mixture 137, is cooled to a temperature of between about 20° C. and about 28° C. in a first crystallizer 261 to form a slurry 263 of purified 2,4'-MDI crystals in a liquid having a composition of about 30% by weight MDI. The slurry 263 enters a first separator 265, where the purified 2,4'-MDI crystals are separated from the liquid. The purified 2,4'-MDI crystals are then heated to a temperature of between about 40° C. and about 50° C. to produce a first purified 2,4'-MDI stream 267. The first purified 2,4'-MDI stream 267 has a fraction containing at least 95% weight of MDI isomers with a content of 4,4'-MDI of less than 8% weight.

The first purified 2,4'-MDI stream 267 enters a second crystallizer 262, where it is cooled to a temperature of between about 20° C. and about 28° C. to form a slurry 264 of purified 2,4'-MDI crystals in a liquid having a composition of about 30% by weight MDI. The slurry 264 enters a second separator 266, wherein the purified 2,4'-MDI crystals are separated from the liquid. The purified 2,4'-MDI crystals are then heated to a temperature of between about 40° C. and about 50° C. to produce a second purified 2,4'-MDI stream 268. As a result, the second purified 2,4'-MDI stream 268 includes a content of 2,4'-MDI of at least 95% by weight. In one example, the second purified 2,4'-MDI stream 268 has a fraction containing at least 99% weight of MDI isomers with a content of 4,4'-MDI of from 0.001% to 5% weight, a content of 2,4'-MDI of from 95% to 99.998% weight, and a content of 2,2'-MDI of from 0.0001% to 0.1% weight. A prepolymer produced from the second purified 2,4'-MDI stream 268 has low viscosity and can be used in applications requiring low 2,2'-MDI content, such as polyurethane film composites and adhesives for product packaging in the food industry.

FIG. 3 is a partial schematic depiction of an apparatus and process 300 according to another embodiment. Many of the steps of the process 300 are identical to those described above with respect to the process 100 depicted in FIG. 1. Thus, identical item numbers are used in FIG. 3 to represent the same processes and apparatus depicted and described with respect to FIG. 1. Referring to FIG. 3, the conventional operations and apparatus of boxes 110 and 120 are the same as those described with respect to FIG. 1.

The crude MDI feedstock 126, containing both MDI isomers and PMDI is heated to a temperature of between about 170° C. and about 260° C. in the heat exchanger 128. In box 130, the lower boiling point components are separated from the higher boiling point components as previously described with respect to FIG. 1. The preheated feedstock enters a distillation column 332. The distillation column 332 includes both a stripping section 333 and a rectification section 335, similar to the stripping section 133 and the rectification section 135 described with respect to FIG. 1.

Similar to that described with respect to FIG. 1, the 2,4'-MDI and 2,2'-MDI are recovered in the stripping section 333 and purified in the rectification section 335 of the distillation column 332. The result yields a 2,4'-MDI rich stream 136 having the same composition as that described with respect to FIG. 1.

The distillation column 332 further includes an integrated side rectification section 352, similar to side rectifier 152. A mixture of the 4,4'-MDI and the PMDI is removed from the distillation column 332 in bottoms 139 and sent to the evaporative reboiler 142 at box 140, similar to that described with respect to FIG. 1. In the evaporative reboiler 142, a portion of the mixture is evaporated and returned to the integrated side rectification section 352 of the distillation column 332. In the integrated side rectification section 352, 4,4'-MDI is separated from traces of PMDI remaining in the vapor. As a result, a purified 4,4'-MDI stream 155 exits the distillation column 332 and is passed through the quench condenser 157 as described with respect to FIG. 1. The operations and apparatus of box 160 as well as the products produced therein are the same as those described with respect to FIGS. 1 and 2.

In summary, embodiments of the present invention provide methods and apparatus for forming mixtures of MDI isomers with a low 2,2'-MDI isomer content and a high 2,4'-MDI isomer content. The resulting mixtures have an increased reactivity and are acceptable in food grade application due to the reduction in primary aromatic amines formed during the curing process. The process and apparatus also include controlling the amount of 4,4'-MDI, which is the most reactive isomer in the mixture allowing use in a wide variety of applications.

While the foregoing is directed to embodiments of the present invention, other and further embodiments of the invention may be devised without departing from the basic scope thereof, and the scope thereof is determined by the claims that follow.

The invention claimed is:

1. A process for the production of a mixture of methylene diphenyl diisocyanate (MDI) isomers, comprising:
   forming methylene diphenyl diamines and polyamines of the diphenylmethane series by reacting aniline and formaldehyde in the presence of an acid catalyst;
   phosgenating the methylene diphenyl diamines and polyamines of the diphenylmethane series to produce a mixture of the MDI isomers and polymeric MDI;
   heating the mixture of the MDI isomers and polymeric MCI to a temperature between about 170° C. and about 260° C.;
   separating from the heated mixture of the MDI isomers and the polymeric MDI a first fraction containing at least 98% by weight of the MDI isomers comprising at least 56% by weight of 2,4'-MDI and 2,2'-MDI based on the total weight of the first fraction, of which a content of 4,4' MDI in the first fraction is from 20% to 43% by weight, a content of 2,4'-MDI of from 56% to 80% by weight, and a content of 2,2'-MDI of from 0.01 to 10% by weight;
   separating from the heated first fraction a second fraction containing at least 99% by weight of the MDI isomers comprising at least 95% by weight of 2,4'-MDI based on the total weight of the second fraction wherein the separating from the first fraction comprises a crystallization operation, and
   after removing the first fraction, a third fraction is separated from the heated mixture of MDI isomers an polymeric MDI using an evaporative reboiler and side rectifier, the third fraction having a content of 4,4'-MDI in the third faction of at last 98% by weight based on the total weight of the third fraction.

2. The process of claim 1, wherein the first fraction includes a content of 4,4'-MDI of from 20% to 43% by weight, a content of 2,4'-MDI of from 56% to 80% by weight, and a content of 2,2'-MDI of from 0.01% to 10% by weight.

3. The process of claim 1, wherein the second fraction includes a content of 4,4'-MDI of from 0.001% to 5% by weight, a content of 2,4'-MDI of from 95% to 99.998% by weight, and a content of 2,2'-MDI of from 0.0001% to 1%.

4. The process of claim 1, wherein the separating from the first fraction comprises sequential crystallization operations.

5. The process of claim 1, wherein a third fraction having a content of 4,4'-MDI of at least 98% by weight based on the total weight of the third fraction is removed from the mixture after removal of the first fraction.

6. The process of claim 5, wherein the third fraction includes a content of 4,4'-MDI of from 98% to 99.99% by weight, a content of 2,4'-MDI of from 0.001% to 2% by weight, and a content of 2,2'-MDI of from 0.001% to 1%.

7. The process of claim 5, wherein polymeric MDI is separated from the third fraction after removal of the first fraction.

8. The process of claim 1, wherein the separating from the first fraction comprises adding a second mixture of MDI isomers containing at least 99% by weight of MDI isomers comprising at least 95% by weight of 2,4'-MDI and 2,2'-MDI based on the total weight of the second mixture.

9. The process of claim 1, wherein separation from the mixture comprises using a distillation column and a side rectifier.

10. The process of claim 1, wherein separation from the mixture comprises using a distillation column having an integrated side rectification section.

\* \* \* \* \*